United States Patent [19]

Okano et al.

[11] 3,950,405
[45] Apr. 13, 1976

[54] TRANS-4-AMINOMETHYLCYCLOHEXANE-1-CARBOXYLIC ACID

[75] Inventors: Atsuji Okano, Otsuka; Shizuo Kadoya, Yokohama; Takeo Naito, Ichikawa; Takaaki Aoyagi, Fujisawa; Masao Shimizu, Otsukanaka, all of Japan

[73] Assignee: Mitsubishi Chemical Industries Ltd., Tokyo, Japan

[22] Filed: June 4, 1969

[21] Appl. No.: 836,196

Related U.S. Application Data

[63] Continuation of Ser. No. 418,325, Dec. 14, 1964, abandoned.

[30] Foreign Application Priority Data

Dec. 24, 1971  Japan................................ 46-69632

[52] U.S. Cl............. 260/514 J; 260/468 J; 424/319
[51] Int. Cl.$^2$........................................ C07C 61/08
[58] Field of Search ................................ 260/514 R

[56] References Cited
FOREIGN PATENTS OR APPLICATIONS
690,537   7/1964   Canada.............................. 260/514

OTHER PUBLICATIONS

Meyer, J. Med. Chem., 15, 641 (1966).
Einhorn; A. et al., Justus Liebigs Annalen der Chemie, Vol. 310, pp. 194–204 (1900).

*Primary Examiner*—Lorraine A. Weinberger
*Assistant Examiner*—P. J. Killos
*Attorney, Agent, or Firm*—Jordan B. Bierman; Linda Bierman; Kenneth J. Stempler

[57] ABSTRACT

A trans isomer of 4-cyanoncyclohexane-1-carboxylic acid or its lower alkyl ester is reduced in a solvent in the presence of a hydrogenating catalyst, and hydrolyzing the produced ester in case the starting trans-isomer is a lower alkyl ester, then the trans-4-aminomethyl-cyclohexane-1-carboxylic acid is recovered from the reaction mixture.

1 Claim, No Drawings

TRANS-4-AMINOMETHYLCYCLOHEXANE-1-CARBOXYLIC ACID

This application is a streamlined continuation of copending application Ser. No. 418,325, filed Dec. 14, 1964, now abandoned.

This invention relates to a process for producing a novel compound, trans-4-aminomethylcyclohexane-1-carboxylic acid. An object of the present invention is to provide a convenient process for producing trans-4-aminomethylcyclohexane-1-carboxylic acid. Another object and advantageous features of the present invention will appear from the following detailed description.

4-Aminomethycyclohexane-1-carboxylic acid has been known as a valuable substance for pharmaceutical use, and it is specifically pointed out in Belgian Pat. No. 617216 that the compound has an antiplasmic effect and is effective on disorders caused by the activated plasmin in vivo. On the other hand, stereochemistry indicates that there can exist cis- and trans-stereoisomers of the compound. However, this has not been confirmed by any papers thus far published, and it has so far been unknown as to which of these isomers the pharmaceutical effect of the compound is attributable to.

So far, 4-aminomethylcyclohexane-1-carboxylic acid has been produced by reducing 4-cyanobenzoic acid or 4-aminomethylbenzoic acid with platinum oxide as a catalyst, as described in Japanese Pat. Nos. 240611 and 242664. However, the resulted product of such a chemical reaction is believed to be a mixture of cis- and trans-stereoisomers. On the other hand, in a paper (Leibig's Annalen der Chemie, vol. 301, p. 194 (1900)) which reported on the synthesis of 4-aminomethylcyclohexane-1-carboxylic acid through hydrogenation of 4-aminomethylbenzoic acid with sodium and amyl alcohol, the resulted product was separated through difference of solubility in methanol into two types of substances, which were named α and β respectively. These two substances, however, are believed to be impure from the standpoint of stereochemistry.

The process of the present invention is represented by the following reaction formula:

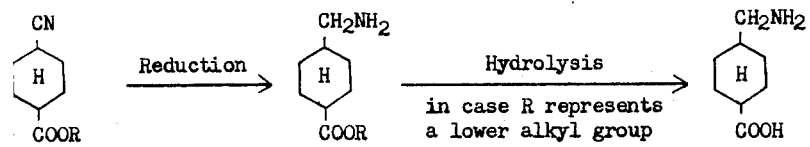

wherein R represents a lower alkyl group or hydrogen atom and the steric relation between the cyano group or the aminomethyl group in the $C_4$-position of the cyclohexane ring and the carboxyl group or its lower alkyl ester group in the $C_1$-position of the same ring indicates a trans-conformation.

In our study of stereoisomers of 4-aminomethylcyclohexane-1-carboxylic acid, the cyano group of trans-4-cyanocyclohexane-1-carboxylic acid or its lower alkyl ester was catalytically reduced to an aminomethyl group, and, in case the carboxyl group had been esterified, it was further hydrolyzed, thereby to produce trans-4-aminomethylcyclohexane-1-carboxylic acid. Cis-4-aminomethylcyclohexane-1-carboxylic acid was similarly produced using cis-4-cyanocyclohexane-1-carboxylic acid or its lower alkyl ester, such as methyl and ethyl ester as a starting material. Both of these stereoisomers are new compounds disclosed for the first time by us. Cis-or trans-4-cyanocyclohexane-1-carboxylic acid or its methyl ester herein used as a starting material is described in the Journal of the American Chemical Society, Vol. 82, p. 2547 (1960). Ethyl cis-or trans-4-cyanocyclohexane-1-carboxylate is a novel compound, and is produced according to the analogous process to that described in said literature. However, there has been published no paper which suggested the possibility of preparing aminomethyl derivatives from the cyano compounds.

In the present invention, trans-4-aminomethylcyclohexane-1-carboxylic acid or its lower alkyl ester is produced with ease by hydrogenating trans-4-cyanocyclohexane-1-carboxylic acid or its lower alkyl ester in a solvent selected from the group consisting of water, aliphatic lower alcohol such as methanol or ethanol and a mixture thereof at a room or an elevated temperature under a normal or increased pressure in the presence of a catalyst selected from the group consisting of platinum oxide, palladium charcoal, palladium black, Raney cobalt and Raney nickel. In this reaction, the solution is preferably made neutral or alkaline by the addition of ammonia or alkylamine such as monoalkylamine, dialkylamine or trialkylamine to prevent the formation of a secondary amine as a by-product. In case trans-4-cyanocyclohexane-1-carboxylic acid is used as a starting material, the reaction solution, after the catalyst was removed, may be passed through a column of ion-exchange resin to purify the product, but this step is not essential. While, in case lower alkyl trans-4-cyanocyclohexane-1-carboxylate is used as a starting material, the produced lower alkyl trans-4-aminomethylcyclohexane-1-carboxylate can be, in practice, converted into trans-4-aminomethylcyclohexane-1-carboxylic acid with ease by immediately hydrolyzing the former with dilute mineral acid such as dilute hydrochloric acid or dilute alkali solution such as sodium or potassium hydroxide solution without isolating and purifying the same. The resulted solution is then passed through a column of ion-exchange resin, this step being essential in this case in order to remove inorganic ions. When mineral acid is used as a hydrolyzing agent, the ion-exchange resin is a weakly basic one, while, when alkali solution is used as a hydrolyzing agent, the ion-exchange resin is a weakly acidic one.

In order to carry out the reaction advantageously on an industrial scale, trans-4-cyanocyclohexane-1-carboxylic acid is hydrogenated at a room temperature under pressure in a hydrous methanol made alkaline by the addition of ammonia water in the presence of Raney nickel, and then the catalyst is filtered and the solvent is removed by distillation. When lower alkyl trans-4-cyanocyclohexane-1-carboxylate is used as a starting material, it is subjected to the same reaction and treatment as above, and the residue is hydrolyzed with dilute hydrochloric acid in a hot water bath to produce trans-4-aminomethyl-cyclohexane-1-carboxylic acid hydrochloride. The reaction solution is passed through a column of a weakly basic ion-exchange resin to obtain trans-4-aminomethylcyclohexane-1-carboxylic acid in an yield of from 85 to 95 percent.

Trans-4-aminomethylcyclohexane-1-carboxylic acid which has the stereo conformation:

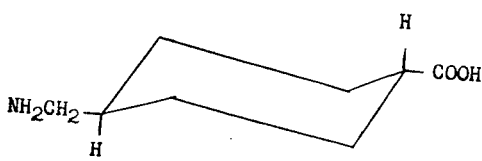

is colorless powder having the melting point of 380° – 390°C (decomp. uncorrect. in air bath) and has characteristic infra-red absorptions at 1637, 1535 and 1383 cm$^{-1}$.

The salts of trans-4-aminomethylcyclohexane-1-carboxylic acid have the following melting points.

| HCl salt | (C$_8$H$_{15}$NO$_2$.HCl) | 238 – 240°C (decomp.) |
|---|---|---|
| HBr salt | (C$_8$H$_{15}$NO$_2$.HBr) | 227 – 229°C (decomp.) |
| Au salt | (C$_8$H$_{15}$NO$_2$.HCl.AuCl$_3$) | 204 – 206°C (decomp.) |
| Pt salt | ((C$_8$H$_{15}$NO$_2$.HCl)$_2$PtCl$_4$) | 254 – 255°C (decomp.) |

Cis-isomer which has the stereo conformation:

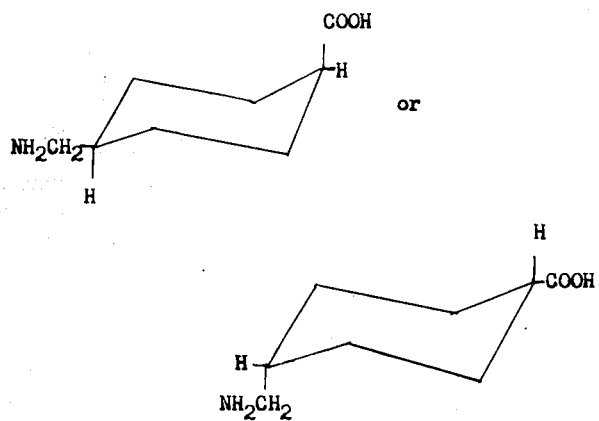

is colorless powder having the melting point of 238° – 242°C (decomp.) and has characteristic infra-red absorptions at 1640, 1565, 1515, 1415 and 1310 cm$^{-1}$.

Trans-4-aminomethylcyclohexane-1-carboxylic acid is soluble in six times volume of water at a room temperature but insoluble in methanol. Furthermore, hydrochloric acid salt of cis-4-aminomethylcyclohexane-1-carboxylic acid is more soluble in methanol than that of trans-4-aminomethylcyclohexane-1-carboxylic acid.

To confirm the stereo conformation of both isomers, the spectra of nuclear magnetic resonance absorption are taken from heavy water solution of samples by using dioxane as internal standard material at room temperature. In this spectrum, trans-4-aminomethylcyclohexane-1-carboxylic acid shows sharp doublet signals at 51 and 56 cps on the higher magnetic field side than that of dioxane, which are signals of methylene group of aminomethyl group, a broad signal having about 30 cps of half value wide at about 95 cps, which is considered a signal of hydrogen atom bound to carbon atom binding the carboxyl group because it transferred by about 10 cps to lower magnetic field side by the addition of hydrochloric acid, and a broad signal having about 60 cps of half-value side at about 130 cps, which is a signal of ring methylene group. Cis-4-aminomethylcyclohexane-1-carboxlic acid shows sharp doublet signals at 45 and 51 cps on the higher magnetic field side than that of dioxane which are signals of methylene group of aminomethyl group, broad signal having about 15 cps of half-value wide at about 85 cps which is considered a signal of hydrogen atom bound to carbon atom binding carboxyl group from the view point that it is transferred by about 20 cps to the lower magnetic field side by the addition of hydrochloric acid, and a broad signal having about 25 cps of half-value wide at about 130 cps, which is a signal of ring methylene group.

In comparison between the spectra of both isomers, the signal of ring methylene group of trans-4-aminomethylcyclohexane-1-carboxylic acid has twice half-value wide as that of cis-4-aminomethylcyclohexane-1-carboxylic acid. And the signal of hydrogen atom bound to carbon atom binding carboxyl group of trans-4-aminomethylcyclohexane-1-carboxylic acid mentioned above exists on the higher magnetic field side and has broader half-value wide than that of cis-4-aminomethylcyclohexane-1-carboxylic acid mentioned above. Accordingly, the hydrogen atom is supposed to be bound axially to cyclohexane ring of trans-4-aminomethylcyclohexane-1-carboxylic acid mentioned above.

It is concluded that trans-4-aminomethylcyclohexane-1-carboxylic acid mentioned above is truly trans-isomer of 4-aminomethylcyclohexane-1-carboxylic acid by the following reasons.

1. Assumed trans-4-aminomethylcyclohexane-1-carboxylic acid is prepared by hydrogenation of trans-4-cyanocyclohexane-1-carboxylic acid.

2. Assumed trans-4-aminomethylcyclohexane-1-carboxylic acid is oxidized by potassium permanganate to give known trans-hexahydroterephthalic acid, while assumed cis-4-aminomethylcyclohexane-1-carboxylic acid gives known cis-hexahydroterephthalic acid by the same procedure.

3. The melting point of assumed trans-4-aminomethylcyclohexane-1-carboxylic acid is higher than that of assumed cis-4-aminomethylcyclohexane-1-carboxylic acid.

4. In the nuclear magnetic resonance spectra, the signal of ring methylene group of assumed trans-4-aminomethylcyclohexane-1-carboxylic acid has twice half-value wide as that of assumed cis-4-aminomethylcyclohexane-1-carboxylic acid.

5. The signal of hydrogen atom bound to carbon atom binding carboxyl group of assumed trans-4-aminomethylcyclohexane-1-carboxylic acid exists on the higher magnetic field side, and has broader half-value wide than that of assumed cis-4-aminomethylcyclohexane-1-carboxylic acid.

6. The infra-red spectrum of assumed trans-4-aminomethylcyclohexane-1-carboxylic acid is more simple than that of assumed cis-4-aminomethylcyclohexane-1-carboxylic acid.

Trans-4-aminomethylcyclohexane-1-carboxylic acid produced by the process of the present invention has a potent inhibitory action on the plasmin system, and also an excellent therapeutic effect on disorders associated with and/or caused by the activated plasmin in vivo, without any accompanying noticeable toxicity when applied.

Some preferred embodiments of the invention will be described in detail wherein the examples given are for the purpose of illustrating preferred embodiments only and not for the purpose of limiting the same.

The present invention is illustrated by the following examples:

Example 1.

In 75 ml of methanol was dissolved 5 g. of trans-4-cyanocyclohexane-1-carboxylic acid. To this solution were added 5 ml of concentrated ammonia water (about 28 %) and 1 g. of Raney nickel developed by a known method.

The mixture was placed in an autoclave and shaken at a room temperature for 4 hours in an atmosphere of hydrogen, the initial pressure of which being 20 kg/cm². After the completion of the reaction, the catalyst was removed by filtration and the filtrate was concentrated under a reduced pressure. The residue was dissolved in water and the solution was passed through a column of a strongly acidic ion-exchange resin ($NH_4$ type), and concentrated under a reduced pressure. The final residue, upon recrystallization from a mixed solution of water and acetone, gave 4.72 g. (yield, 92 %) of trans-4-aminomethylcyclohexane-1-carboxylic acid in the form of five needles, mp. 380° - 390°C (decomp. uncorrect in air bath)

Analysis for $C_8H_{15}O_2N$. Calculated (%) C 61.12, H 9.62, N 8.91. Found (%) C 61.20, H 9.65, N 8.63.

Example 2.

In 75 ml of methanol was dissolved 5 g. of methyl trans-4-cyanocyclohexane-1-carboxylate. The solution was added with 5 ml of concentrated ammonia water (about 28 %) and subjected to a hydrogenation reaction according to the same procedure as described in Example 1.

The catalyst was removed by filtration and the filtrate was concentrated under a reduced pressure. The residue was added with 100 ml of 2N-hydrochloric acid and hydrolyzed with heating in a water bath kept at 95°C for 30 minutes. The reaction solution was concentrated under a reduced pressure, and the residue was dissolved in water. The chlorine ions were eliminated by passing the solution through a column of slightly basic ion-exchange resin IR-4B(OH type). The resulted aqueous solution was concentrated and the residue was recrystallized from a mixed solution of water and acetone to obtain 4.3 g. (yield, 92 %) of fine needles of trans-4-aminomethylcyclohexane-1-carboxylic acid, m.p. 380° - 390°C (decomp. uncorrect in air bath).

Example 3.

5.0 g. of ethyl trans-4-cyanocyclohexane-1-carboxylate (b.p. 113° - 115°C/5mmHg) was treated in the same manner as described in Example 2. Upon recrystallization the resulted product gave 4.0 g. (yield, 85 %) of fine needles, m.p. 380° - 390°C (decomp.).

Example 4.

In 75 ml of 70 % hydrous methanol, 5 g of methyl trans-4-cyanocyclohexane-1-carboxylate was dissolved. The solution, with the addition of 3 g. of triethylamine, was subjected to the same reaction and treatment as described in Example 2. The resulted product, upon recrystallization from a mixture of water and acetone, gave 4 g. of fine needles of trans-4-aminomethylcyclohexane-1-carboxylic acid.

Example 5.

In 75 ml of ammonia water containing 0.033 mole of ammonia, 5 g. of trans-4-cyanocyclohexane-1-carboxylic acid was dissolved. To this solution, 0.5 g of Raney cobalt developed by a known method was added. The mixture was subjected to the same reaction and treatment as described in Example 1, and 4 g. of trans-4-aminomethylcyclohexane-1-carboxylic acid was obtained.

Example 6.

In 75 ml of ammonia water containing 0.033 mole of ammonia, 5 g. of trans-4-cyanocyclohexane-1-carboxylic acid was dissolved. To this solution, 0.5 g. of Raney cobalt developed by a known method was added. The whole mixture was shaken in an atmosphere of hydrogen under a normal pressure for about 5 hrs. until 0.066 mole of hydrogen had been absorbed. The reduction product was treated as described in Example 1, and 4.1 g. of trans-4-aminomethylcyclohexane-1-carboxylic acid was obtained.

Example 7.

5 g. of trans-4-cyanocyclohexane-1-carboxylic acid was dissolved in 130 ml of methanol. To this solution, 5 g. of 10 % Pd-charcoal was added and the mixture was shaken in an atmosphere of hydrogen under a normal pressure for about 8 hours until 0.066 mole of hydrogen was absorbed. The reaction product was treated as described in Example 1, and 3.5 g. of trans-4-aminomethylcyclohexane-1-carboxylic acid was obtained.

What is claimed is:
1. Trans-4-aminomethylcyclohexane-1-carboxylic acid.

* * * * *

UNITED STATES PATENT OFFICE
CERTIFICATE OF CORRECTION

PATENT NO. : 3950405
DATED : April 13th, 1976.
INVENTOR(S) : Atsuji Okano, Shizuo Kadoya, Takeo Naito
Takaaki Aoyagi and Masao Shimizu It is certified that error appears in the above-identified patent and that said Letters Patent are hereby corrected as shown below:

Cover sheet item [73] after "Tokyo, Japan"
insert -- Daiichi Seiyaku Co. Ltd.,
　　　　Tokyo, Japan --

Cover sheet item [30] cancel "Dec. 24, 1971
Japan...........46-69632"
insert -- Dec. 24, 1963 Japan.......38-69632 --

Signed and Sealed this

Tenth Day of August 1976

[SEAL]

Attest:

RUTH C. MASON
Attesting Officer

C. MARSHALL DANN
Commissioner of Patents and Trademarks